| United States Patent [19] | [11] | 4,414,220 |
|---|---|---|
| Belletire | [45] | Nov. 8, 1983 |

[54] ORGANIC DIAMINE THERAPEUTIC COMPOSITIONS

[75] Inventor: John L. Belletire, Madison, Wis.

[73] Assignee: Pfizer Inc., New York, N.Y.

[21] Appl. No.: 353,514

[22] Filed: Mar. 1, 1982

Related U.S. Application Data

[62] Division of Ser. No. 123,063, Feb. 20, 1980, Pat. No. 4,333,932, which is a division of Ser. No. 952,302, Oct. 18, 1978, Pat. No. 4,220,650.

[51] Int. Cl.³ .................. A61K 31/445; C07D 401/10
[52] U.S. Cl. .................................... 424/267; 546/140;
546/148; 546/149; 546/191; 546/194; 546/208; 546/201; 546/229; 546/230; 546/232; 546/264; 546/273; 546/281; 546/304; 546/312; 548/465; 548/470; 548/482; 548/524; 548/566; 564/388; 424/244; 424/246; 424/248.56; 424/258; 424/263; 424/274; 424/304; 424/330; 544/39; 544/60; 544/62
[58] Field of Search ...................... 544/59, 60, 62, 78, 544/86, 87, 124, 128, 129, 111, 143, 141, 162, 163; 260/239 B, 465 E; 546/140, 148, 149, 191, 194, 208, 201, 229, 230, 232, 264, 273, 281, 304, 312; 548/465, 470, 482, 524, 566; 564/388; 424/244, 248.56, 258, 263, 267, 274

[56] References Cited

PUBLICATIONS

Knollmueller "Monatshefte fur Chemie", vol. 105, No. 1, pp. 114-122 (1974).

*Primary Examiner*—Robert T. Bond
*Attorney, Agent, or Firm*—Connolly and Hutz

[57] ABSTRACT

A series of organic diamine base compounds derived from either an aromatic, alicyclic or heterocyclic ring and possessing, for the most part, an intervening methylene group between the ring and the aforesaid basic moiety have been prepared, including their pharmaceutically acceptable acid addition salts as well as oral pharmaceutical compositions containing same. These particular compounds are found to be useful in therapy as oral hypoglycemic agents. Preferred member compounds include 1,1'-[1,2-phenylenebis(methylene)]bis-piperidine, 2,3-dihydro-2-[2-(1-piperidinomethyl)-phenylmethyl]-1H-isoindole and 2,3-dihydro-2-[2-(4-morpholinomethyl)phenylmethyl]-1H-isoindole. Alternate methods of preparation are provided and the two principal synthetic routes leading to these compounds are described in some detail.

15 Claims, No Drawings

ORGANIC DIAMINE THERAPEUTIC COMPOSITIONS

CROSS REFERENCE TO RELATED APPLICATIONS

This application is a division of application Ser. No. 123,063 filed Feb. 20, 1980, now U.S. Pat. No. 4,333,932 which in turn is a division of application Ser. No. 952,302 filed Oct. 18, 1978 and now U.S. Pat. No. 4,220,650.

BACKGROUND OF THE INVENTION

This invention relates to new and useful organic diamine hypoglycemic agents. More particularly, it is concerned with a series of organic diamine base compounds and their pharmaceutically acceptable acid addition salts, which are useful in therapy as oral hypoglycemic agents for the treatment of diabetes. The invention also includes various novel oral pharmaceutical compositions as well as a new method of therapy as being well within its scope.

In the past, various attempts have been made by numerous investigators in the specialized field of synthetic organic medicinal chemistry to obtain new and better oral hypoglycemic agents. For the most part, these efforts have principally involved the synthesis and testing of various heretofore new and unavailable organic compounds, particularly in the area of the sulfonylureas, in an endeavor to determine their ability to lower blood sugar (i.e., glucose) levels to a substantially high degree when given by the oral route of administration. However, in the search for newer an still more effective antidiabetic agents, far less is known about the effect of non-sulfonylureas in this area, such as various organic base compounds like primary, secondary or tertiary-alkyl and/or cycloalkylamines or ring-nitrogen compounds like the indoles and their side-chain derivatives. For instance, in U.S. Pat. Nos. 3,459,767 and 3,542,927 certain aminomethylindole compounds are reported to be active as hypoglycemic agents, while others are not. On the other hand, in U.S. Pat. No. 3,564,012 several 5,7-dimethyoxytryptamines are found to be very useful in this area, while the corresponding 5-methoxy and 7-methoxytryptamines are only useful as analeptic agents (see British Pat. Nos. 974,893, 974,894 and 974,895). Moreover, U.S. Pat. Nos. 3,510,492, 3,510,493, 3,647,804 and 3,651,232 all report on various 2-anilino and aminomethylcycloalkylamines that are alleged to be useful as oral antidiabetic agents, but none of these compounds possess any outstanding clinical advantages over that of either chlorpropamide or tolbutamide when used in this connection.

SUMMARY OF THE INVENTION

In accordance with the present invention, it has now been rather surprisingly found that various organic diamine base compounds (i.e., non-sulfonylureas) derived from either an aromatic, alicyclic or heterocyclic ring and possessing, for the most part, an intervening methylene group between the ring and the aforesaid basic moiety are extremely useful when employed in therapy as oral hypoglycemic agents for the treatment of diabetic subjects. More particularly, the novel oral pharmaceutical composition of this invention all comprise a pharmaceutically acceptable carrier and an effective blood sugar lowering amount of an oral hypoglycemic agent, said agent being a compound selected from the group consisting of organic diamine bases of the formulae:

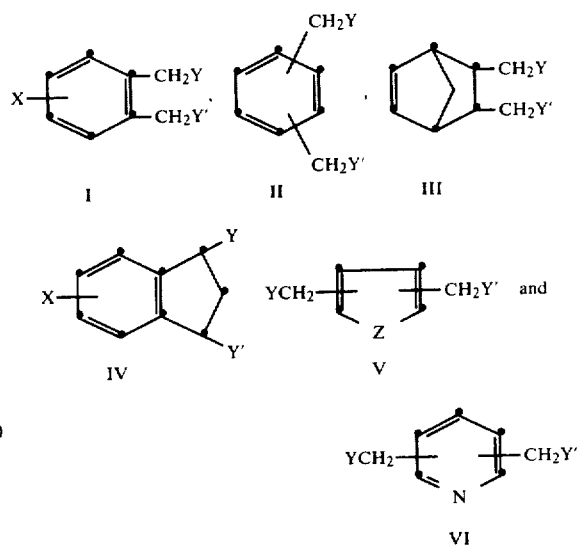

and the pharmaceutically acceptable acid addition and quaternary ammonium salts thereof, wherein X is a member selected from the group consisting of hydrogen, fluorine, chlorine, bromine, nitro, cyano, lower alkyl and lower alkoxy (each having from one to four carbon atoms), said X being other than hydrogen when the organic diamine base is a compound of formula I; Y and Y' are each a member selected from the group consisting of amino, lower N-monoalkylamino, lower N,N-dialkylamino (each alkyl having from one to four carbon atoms), pyridylamino, pyrrolidino, piperidino, homopiperidino, morpholino, thiomorpholino, 2,3-dihydroisoindolyl and 1,2,3,4-tetrahydroisoquinolyl; and Z is oxygen or sulfur. It is to be understood that the use of the term "diamine" in this connection refers to the nature of the side-chain functional groups in the definition of Y and Y', etc. rather than the total number of nitrogen atoms in the molecule. These compounds are all useful in lowering blood sugar levels when given by the oral route of administration, i.e., they are useful as oral hypoglycemic agents, and are particularly useful as oral antidiabetic agents in view of their ability to release insulin in the presence of even significant amounts of glucose in the body. The latter so-called "improved toleration of glucose" effect is a most desirable property, not found even in the sulfonylureas.

More specifically, the novel compounds of this invention are those organic diamines of formula I where X is other than hydrogen, and those of formula II where Y is pyridylamino and Y' is other than the same said group. Additionally, the indan-ring compounds of formula IV and the pyridine-ring compounds of formula VI are also all novel compounds.

Accordingly, the novel compounds of formula I comprise organic diamine bases of the formula:

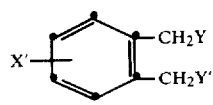

and the pharmaceutically acceptable acid addition and quaternary ammonium salts thereof, wherein X' is a member selected from the group consisting of fluorine, chlorine, nitro, cyano and lower alkoxy; and Y and Y' are each a member selected from the group consisting of amino, lower N-monoalkylamino, lower N,N-dialkylamino, pyridylamino, pyrrolidino piperidino, homopiperidino, morpholino, thiomorpholino, 2,3-dihydroisoindolyl and 1,2,3,4-tetrahydroisoquinolyl.

The novel compounds of formula II comprise organic diamine bases of the formula:

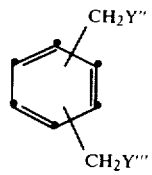

and the pharmaceutically acceptable acid addition and quaternary ammonium salts thereof, wherein Y'' is pyridylamino and Y''' is a member selected from the group consisting of amino, lower-N-monoalkylamino, lower N,N-dialkylamino, pyrrolidino, piperidino, homopiperidino, morpholino, thiomorpholino, 2,3-dihydroisoindolyl and 1,2,3,4-tetrahydroisoquinolyl.

The novel compounds of formula IV comprise organic diamine bases of the formula:

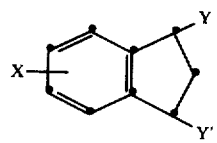

and the pharmaceutically acceptable acid addition and quaternary ammonium salts thereof, wherein X is a member selected from the group consisting of hydrogen, fluorine, chlorine, bromine, nitro, cyano, lower alkyl and lower alkoxy; and Y and Y' are each a member selected from the group consisting of amino, lower N-monoalkylamino, lower N,N-dialkylamino, pyridylamino, pyrrolidino, piperidino, homopiperidino, morpholino, thiomorpholino, 2,3-dihydroisoindolyl and 1,2,3,4-tetrahydroisoquinolyl.

Lastly, the novel compound of formula VI comprise organic diamines bases of the formula:

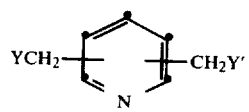

and the pharmaceutically acceptable acid addition and quaternary ammonium salts thereof, wherein Y and Y' are each a member selected from the group consisting of amino, lower N-monoalkylamino, lower N,N-dialkylamino, pyridylamino, pyrrolidino, piperidino, homopiperidino, morpholino, thiomorpholino, 2,3-dihydroisoindolyl and 1,2,3,4-tetrahydroisoquinolyl.

Of especial interest in this connection are such typical and preferred member compounds of the invention as 1,1'-[1,2-phenylenebis(methylene)]bispiperidine, 2,3-dihydro-2-[2-(1-piperidinomethyl)phenylmethyl]-1H-isoindole and 2,3-dihydro-2-[2-(4-morpholinomethyl)-phenylmethyl]-1H-isoindole, and their pharmaceutically acceptable acid addition salts, such as the hydrochlorides and maleates, for example. These particular compounds are all highly potent as regards their hypoglycemic activity, in addition to being extremely effective in releasing insulin to the body at both high and low glucose levels (i.e., they exhibit a marked-improvement in glucose tolerance). In this connection, it should also be noted that 2,3-dihydro-2-[2-(4-morpholinomethyl)-phenylmethyl]-1H-isoindole is a novel compound per se.

DETAILED DESCRIPTION OF THE INVENTION

In accordance with one process employed for preparing the organic diamine compounds of this invention, a corresponding dihalo compound having the same general structural formula as those previously indicated except that a halogen atom is attached directly to the non-aromatic portion of the molecule instead of Y or Y', etc., and one wherein the halogen atom is preferably either chlorine or bromine, is treated with at least a dimolar amount of the appropriate amine base of the formula YH or Y'H, etc., to yield the desired diamine final product. The particular reaction is normally carried out by using an excess of the amine base with respect to the required dimolar reaction ratio, since this serves to shift the reaction equilibrium to the product side of the equation. In addition, the excess amine can also function as a solvent for the reaction, with a preferred excess for these purposes being from about three to about ten moles of amine per one mole of dihalo compound. On the other hand, a reaction-inert aprotic organic solvent may also be used for the reaction and this would ordinarily entail employment of an aromatic hydrocarbon solvent such as benzene, toluene and xylene, or a cyclic ether such as dioxane and tetrahydrofuran, or a lower dialkyl sulfoxide such as dimethyl and diethyl sulfoxide, or a lower alkanol like methanol, ethanol or isoamyl alcohol, etc. or even a N,N-dialkyl lower alkanoamide such as N,N-dimethylformamide, N,N-dimethylacetamide, N,N-diethyl formamide and the like. The temperature at which the reaction can be conducted varies widely within the temperature range of from about 50° C. up to about 200° C. for a period of about five to about 96 hours.

In connection with a more detailed consideration of the above described condensation process, a preferred time and temperature for the reaction would be about 80°–110° C. for a period of approximately 16–24 hours. In the case where a particular solvent is used and/or the boiling point of the amine is below the desired reaction temperature range, it is often customary in practice to employ a sealed pressure bottle as the proper vessel in which to conduct the reaction. Upon completion of same, recovery of the desired product is then readily effected by any number of conventional means. For instance, the solvent is evaporated from the reaction mixture and the crude concentrate or resulting solid residue is thereafter triturated with ethyl acetate or another similar organic solvent, followed by further purification of the product (if necessary) via crystallization, recrystallization and column chromatography, etc. In this way, high yields of the pure organic diamine (i.e., the desired final product) are easily obtained. It should also be noted in this connection that the dihalo organic compounds employed as starting materials and the amines (YH) employed as reagent in this reaction are, for the most part, known compounds or else they are easily be prepared by those skilled in the art from more readily available starting materials using the standard procedures of organic chemistry.

An alternate and equally facile route to the production of the organic diamine base compounds of this invention involves reducing the corresponding carboxamides (these are either known or also easily prepared by those skilled in the art from the corresponding carboxylic acids). This particular reduction step is preferably accomplished in the presence of a complex metal hydride and yields the same desired diamine final products that have already been described elsewhere in the specification. More particularly, an organic diamide having the same general structural formula as those previously presented for the amines but wherein a carboxamide functional group is attached directly to the non-aromatic portion of the molecule instead of Y or Y', etc., is subjected to the selective reductive action of lithium aluminum hydride or diborane in an ether-type organic solvent, or to an organo metallic complex like diisobutyl aluminum hydride in an aromatic hydrocarbon solvent, such as benzene or toluene, at a temperature ranging from well below room temperature (say, e.g., $-78°$ C.) up to the reflux point of the reaction mixture. In the case where the reaction is carried out with lithium aluminum hydride or a similar metal hydride, such as magnesium aluminum hydride, the ether-type solvent is preferably one that is chosen from the class which includes diethyl ether, di-isopropyl ether, di-n-butyl ether, tetrahydrofuran, dioxane and dimethylcellosolve, etc. Similar solvents can also be used with diborane although the use of tetrahydrofuran is definitely preferred in the latter connection. In general, the reduction step in the ether-type organic solvent is usually carried out at a temperature ranging from about 0° C. up to about 120° C. or at least up to the reflux temperature of the reaction mixture if the boiling point of the solvent employed is below the upper limit of the aforesaid range. The time of reaction will necessarily vary from about three to about 96 hours. Upon completion of same, the resulting diamine is then in the form of a complex salt which is thereafter slowly decomposed with water or with any other commonly used aqueous system that is normally employed for these purposes, e.g., aqueous hydrochloric acid in the case of diborane and aqueous sodium or potassium hydroxide or even aqueous disodium tartrate (or sodium potassium tartrate) in the case of lithium aluminum hydride. Recover of the desired product from the resulting organic (ethereal) layer once decomposition of the above complex salt has already taken place can then be brought about by any number of standard procedures well known to those skilled in the art. For example, the filtered and subsequently washed and dried ethereal layer can be concentrated under reduced pressure to afford the crude product as residual material, which is then further purified by such means as recrystallization from a suitable solvent and/or column chromatography and the like.

As regards those organic diamine base compounds of the invention where Y' (or Y''') in the aforesaid structural formulae is specifically 2,3-dihydroisoquinolyl, these are preferably prepared by subjecting the corresponding monocarboxamide of the same general structural formula as those previously presented for the amines except that a carboxamido functional group is now directly attached to the non-aromatic portion of the molecule instead of Y (or Y''), and Y' (or Y''') is already 2,3-dihydroisoquinolyl, to the selective reductive action of a complex metal hydride such as lithium aluminum hydride in the same manner as that described previously. In this connection, it should also be noted that the monocarboxamide compounds required as starting materials for this reaction are either known compounds or else easily prepared by those skilled in the art starting from the corresponding known monocarboxylic acids such as 2,3-dihydro-2-(2-carboxphenylmethyl)-1H-isoindole [J. Bornstein et al., *Journal of the American Chemical Society*, Vol. 78, p. 83 (1956)], for example. In this way, an elegant overall method is provided for the preparation of those organic diamine base compounds that are "unsymmetrical" in structure, i.e., where the amine moieties (Y and Y', etc.) are not the same but different and Y' is specifically 2,3-dihydroisoquinolyl.

As regards those organic diamine base compounds of the invention where at least one of Y and Y' in structural formulae I-II and V-VI is specifically amino, these are preferably prepared by selectively reducing in the same manner as described before i.e., by using complex metal hydrides, the corresponding cyano compound required for the present purposes at hand. For instance, a compound having the same general structural as those previously presented for the diamine except that a cyano group is directly attached to the ring instead of either $-CH_2Y$ or $-CH_2Y'$ (or both) is converted, via this particular method of reduction, to the corresponding compound where at least one of Y and Y' is specifically amino. The cyano compounds, required as starting materials for the reaction, are either known or else easily prepared by those skilled in the art using conventional methods of synthesis. For example, the mono cyano compounds, like 1-(2-cyanophenylmethyl)hexamethyleneimine, are usually prepared by condensing the corresponding halo compound (e.g., α-bromo-o-tolunitrile) with the appropriate amine.

Inasmuch as those organic diamine base compounds of the invention which possess structural formulae III-IV are capable of existing in both cis- and trans-isomeric forms, it is to be understood that the present invention clearly contemplates both as being well within its scope, in addition to the various cis/trans-isomeric mixtures which are necessarily obtained during the course of the organic synthesis leading to said compounds. For instance, a pure geometrical isomer may be obtained by simply subjecting the aforesaid mixture to either fractional crystallization or to column chromatography, etc.; for the present purposes at hand. Alternatively, the geometrical isomer in question may be readily prepared by merely using the appropriate pure isomer as starting material (if available) in the foregoing series of reactions hereinbefore described, followed by further purification of the product if absolutely necessary.

The pharmaceutically acceptable acid addition salts of the organic diamine base compounds of this invention are prepared by simply treating the aforementioned organic bases with various mineral and organic acids which form non-toxic acid addition salts having pharmacologically acceptable anions, such as the hydrochloride, hydrobromide, hydroiodide, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts. For instance, the salt-formation step may be carried out by using a substantially equimolar amount of the appropriate acid in an aqueous solvent medium or in a suitable organic solvent such as methanol or ethanol. Upon careful evaporation of the solvent, the solid salt product is readily obtained.

Suitable quaternary ammonium salts of the various organic diamine base compounds of this invention include those which are obtained by reacting the various organic diamine bases of the foregoing type with a pharmaceutically acceptable organic halide, such as methyl iodide, ethyl bromide, n-propyl iodide, allyl chloride, n-hexyl bromide, cyclopentyl iodide, benzyl chloride, m-xylyl bromide, p-chlorobenzhydryl chloride and the like, or with an equally acceptable sulfuric acid lower alkyl ester or an arylsulfonic acid lower alkyl ester, such as dimethyl sulfate, dimethyl sulfite, diethyl sulfate, methyl benzenesulfonate, ethyl p-toluenesulfonate and the like.

As previously indicated, the organic diamine base compounds of this invention are all readily adapted to therapeutic use as oral hypoglycemic agents, in view of their ability to lower the blood sugar levels of both diabetic and non-diabetic subjects to a statistically significant degree. For instance, 1,1'-[1,2-phenylenebis(methylene)]bispiperidine (as the dimaleate salt), a typical and preferred agent of the present invention, has been found to consistently lower blood sugar levels in the fasted diabetic (i.e., hyperglycemic) rat to a statistically significant degree when given by the intraperitoneal route of administration at dose levels ranging from 25 mg./kg. to 100 mg./kg., respectively, without showing any substantial signs of toxic side effects. The other compounds of this invention also cause similar results. Furthermore, all the herein described compounds of this invention can be administered orally, for the present purposes at hand, without causing any significant untoward pharmacological side reactions to occur in the subject to whom they are so administered. In general, these compounds are ordinarily administered at dosage levels ranging from about 0.2 mg. to about 25 mg. per kg. of body weight per day, although variations will necessarily occur depending upon the condition and individual response of the subject being treated and the particular type of oral pharmaceutical formulation chosen.

In connection with the use of the organic diamine base compounds of this invention for the treatment of diabetic subjects, it is to be noted that they may be administered either alone or in combination with pharmaceutically acceptable carriers and that such administration can be carried out in both single and multiple dosages. More particularly, the novel compounds of the invention can be administered in a wide variety of different dosage forms, i.e., they may be combined with various pharmaceutically acceptable inert carriers in the forms of tablets, capsules, lozenges, troches, hard candies, powders, aqueous suspension, elixirs, syrups and the like. Such carriers include solid diluents or fillers, sterile aqueous media and various non-toxic organic solvents, etc. Moreover, such oral pharmaceutical compositions can be suitably sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca, starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection whould also include the high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as hypoglycemic agents, is determined by their ability to lower blood sugar levels in the fasted hyperglycemic rat when tested therein for such purposes according to the procedure described by W. S. Hoffman, as reported in the *Journal of Biological Chemistry*, Vol. 120, p. 51 (1937). The latter method measures directly the amount of glucose in the blood at any given time and from this, the maximum percent decrease in blood sugar can be readily calculated and reported as hypgolcyemic activity per se. In this way, the present organic diamine base compounds are shown to markedly reduce the blood sugar levels of non-anesthetized hyperglycemic rats when administered to them at dose levels as low as 25 mg./kg.

Preparation A

In a 1-liter one-necked, round-bottomed reaction flask equipped with reflux condenser, nitrogen inlet tube and magnetic stirrer, there were placed 25.0 g. (0.094 mole) of α,α'-dibromo-o-xylene and 100 g. (1.176 mole) of piperidine dissolved in 200 ml. of benzene. The resulting mixture was then stirred as a clear solution at room temperature (~25° C.) for a period of several hours, followed by heating under reflux for a period of 48 hours. At the end of this time, the reaction mixture (now in the form of a tan suspension) was cooled to room temperature and diluted with 500 ml. of ethyl acetate, followed by washing with water (five times) and drying over anhydrous magnesium sulfate. After removal of the drying agent by means of filtration and the volatile liquid material by means of evaporation under reduced pressure, there was obtained a clear viscous brown oil which amounted to 12.3 g. (48%) of impure 1,1'-[1,2-phenylenebis(methylene)]bispiperidine as the free base compound.

The above crude oil (12.3 g.) was then taken up in 100 ml. of diethyl ether and slowly poured into a 2-liter wide-mouthed Erlenmeyer flask containing 35.0 g. (0.302 mole) of maleic acid dissolved in 100 ml. of diethyl ether, while maintaining constant agitation throughout the course of the addition step with the aid of a magnetic stirrer. The resulting white semi-solid mixture was then granulated over a period of two hours, and the supernatant liquid (i.e., diethyl ether)

was subsequently discarded and replaced with ca. 200 ml. of isopropyl alcohol. The latter mixture was thereafter heated to a gentle reflux to afford a solution that was subsequently concentrated via a water-bath to about two-thirds of its original volume. On cooling to room temperature overnight (~16 hours), there was obtained a fine white deposit of the dimaleate salt in microcrystalline form. Recrystallization of the latter material from fresh isopropyl alcohol then gave 23.0 g. (47%) of analytically pure 1,1'-[1,2-phenylenebis(methylene)]bispiperidine dimaleate, m.p. 151°–153° C.

Anal. Calcd. for $C_{18}H_{28}N_2.2C_4H_4O_4$: C, 61.89; H, 7.19; N, 5.55. Found: C, 62.16; H, 7.23; N, 5.89.

A sample of the pure diamaleate salt was then converted back to the free base compound by dissolution in water, followed by the addition of 3 N aqueous potassium hydroxide to the solution until the pH of the resulting mixture became strongly basic in character. Upon extraction of the latter basified solution with chloroform, followed by drying of the organic extract over anhydrous magnesium sulfate and filtering, there was obtained a clear organic solution (as filtrate) that was subsequently concentrated in vacuo to afford a colorless viscous oil. The latter material proved to be pure 1,1'-[1,2-phenylenebis(methylene)]bispiperidine as attested to by mass spectroscopy and nuclear magnetic resonance data.

Preparation B

The procedure described in Preparation A was repeated except that 6.5 g. (0.0246 mole) of α,α'-dibromo-m-xylene and 25 g. (0.294 mole) of piperidine were reacted in the absence of a solvent (other than excess piperidine) by heating the reaction mixture in a dry 100 ml. similarly-equipped, round-bottomed reaction flask at the reflux point for a period of 24 hours. In this manner, there was obtained a 4.4 g. (66%) yield of crude 1,1'-[1,3-phenylenebis(methylene)]bispiperidine in the form of a viscous orange oil.

The above crude oil (4.4 g.) was then diluted with 100 ml. of diethyl ether and the resulting solution filtered to remove a trace of insoluble impurities. The clear filtrate was then added to a filtered solution of maleic acid (6.0 g.; 0.0517 mole) in diethyl ether to afford a copious precipitate, which was subsequently stirred for several hours in order to effect granulation. The supernatant ether liquid was thereafter removed by means of decantation and the remaining white solid material was subsequently recrystallized twice from isopropyl alcohol to afford analytically pure 1,1'-[1,3-phenylenebis(methylene)]bispiperidine dimaleate, m.p. 128°–129° C. The yield of pure salt amounted to 3.0 g. (30%).

Anal. Calcd. for $C_{18}H_{28}N_2.2C_4H_4O_4$: C, 61.89; H, 7.19, N, 5.55. Found: C, 61.74; H, 7.16; N, 5.30.

A sample of the pure dimaleate salt was then converted back to the free base compound in the same manner as that described in Preparation A to afford a colorless viscous oil, which proved to be pure 1,1'-[1,3-phenylenebis(methylene)]bispiperidine as attested to by both mass spectroscopy and nuclear magnetic resonance data.

Preparation C

The procedure described in Preparation A was repeated except that 6.5 g. (0.0246 mole) of α,α-dibromo-p-xylene and 25 g. (0.294 mole) of piperidine were reacted in the absence of a solvent (other than excess piperidine) by cautiously adding the aforesaid dibromoxylene reagent in six separate portions to the well-stirred piperidine component contained in a dry 100 ml. round-bottomed reaction flask (similarly equipped as before). In each specific instance, an exothermic reaction ensued. When the final reaction mixture had cooled to room temperature (~25° C.), a heating bath was applied and the resulting pale tan suspension was heated to the reflux point and maintained at said temperature for a period of approximately 16 hours (overnight). At the end of this time, the spent mixture was cooled to room temperature and the resulting semisolid mass was worked-up in essentially the same manner as the tan suspension in Preparation A to afford (after removal of the volatiles) 5.7 g. (85%) of crude, 1,1'-[1,4-phenylenebis(methylene)]bispiperidine in the form of a low-melting crystalline solid (m.p. 82°–88° C.). One low temperature recrystallization of the latter material from n-hexane then gave analytically pure 1,1'-[1,4-phenylenebis(methylene)]bispiperidine, m.p. 86°–88° C. The yield of pure base amounted to 4.8 g. (72%).

Anal. Calcd. for $C_{18}H_{28}N_2$: C, 79.36; H, 10.36; N, 10.28. Found: C, 79.13; H, 10.05; N, 10.24.

Preparation D

The procedure described in Preparation A was repeated except that 3.0 g. (0.0114 mole) of α,α-dibromo-o-xylene and 20.0 g. (0.281 mole) of pyrrolidine were reacted in the absence of a solvent (other than excess pyrrolidine) by cautiously adding the aforesaid dibromoxylene reagent in four separate portions to the pyrrolidine component contained in a dry 100 ml. round-bottomed reaction flask (similarly equipped as before). The resulting amber-colored suspension was then heated at the reflux point overnight (~16 hours), cooled to room temperature (~25° C.) and worked-up in essentially the same manner as the corresponding tan suspension in Preparation A to afford (after removal of the solvent) a pale brown viscous oil which amounted to 2.5 g. (81%) of crude 1,1'-[1,2-phenylenebis(methylene)]bispyrrolidine (as the free base compound).

The above crude oil (2.5 g.) was then taken up in 100 ml. of diethyl ether and added in a slow stream to 4.5 g. (0.038 mole) of maleic acid dissolved in diethyl ether (the latter solution was first filtered before use). In this way, there was ultimately obtained a fine white crystalline precipitate consisting of the crude dimaleate salt which was subsequently isolated by means of decantation of the supernatant ether layer. Two recrystallizations of the latter material from isopropyl alcohol then gave analytically pure 1,1'-[1,2-phenylenebis(methylene)]bispyrrolidine dimaleate, m.p. 146°–147.5° C. The yield of pure salt amounted to 2.0 g. (36%).

Anal. Calcd. for $C_{17}H_{26}N_2.2C_4H_4O_4$: C, 60.49; H, 6.77; N, 5.88. Found: C, 60.18; H, 6.81; N, 6.27.

A sample of the pure dimaleate salt was converted back to the free base compound in the same manner as that described in Preparation A to afford a colorless crystalline solid, which proved to be pure 1,1'-[1,2-phenylenebis(methylene)]bispyrrolidine (m.p. 35°–41° C.) as attested to by mass spectroscopy, infrared absorption spectra and nuclear magnetic resonance data.

Preparation E

The procedure described in Preparation A was repeated except that 3.0 g. (0.0114 mole) of α,α-dibromo-o-xylene and 25.0 g. (0.287 mole) of morpholine were reacted in the absence of a solvent (other than excess morpholine) to afford a crude colorless oil, which amounted to 3.0 g. (63%) of impure 4,4'-[1,2-phenylenebis(methylene)]bismorpholine as the free base compound.

The above crude oil (3.0 g.) was then dissolved in 100 ml. of diethyl ether and added slowly to a filtered solution of maleic acid (5.0 g., 0.043 mole) dissolved in 300 ml. of diethyl ether. A white hygroscopic precipitate soon formed and this was subsequently recovered after the supernatant ether liquid was first removed by means of decantation. The crude dimaleate salt thus obtained was then dissolved in water (50 ml.) and converted back to the free base compound in essentially the same manner as that described in Preparation A (except that methylene chloride was used as the solvent for extraction instead of chloroform) to afford a crystalline white solid (m.p. 35° C.), which proved to be crude 4,4'-[1,2-phenylenebis(methylene)]bismorpholine (yield, 2.0 g.) Two low temperature recrystallizations of the latter material from n-hexane then gave 1.3 g. (41%) of analytically pure 4,4'-[1,2-phenylenebis(methylene)]bismorpholine, m.p. 47°-48.5° C.

Anal. Calcd. for $C_{16}H_{24}N_2O_4$: 69.53; H, 8.75; N, 10.14. Found: C, 69.37; H, 8.68; N, 10.18.

Preparation F

The procedure described in Preparation A was repeated except that 6.5 g. (0.0246 mole) of α,α-dibromo-p-xylene and 30 g. (0.422 mole) of pyrrolidine were reacted in the absence of a solvent (other than excess pyrrolidine) by cautiously adding the dibromoxylene in five separate portions to the pyrrolidine component contained in a dry 250 ml. round-bottomed reaction flask (similarly equipped as before). The resulting reaction mixture was then stirred at room temperature (~25° C.) for a period of one hour, followed by heating at the reflux point for a period of four hours and then stirred once again at room temperature overnight (~16 hours). At this point, the spent mixture was worked-up in essentially the same manner as the corresponding tan suspension in Preparation A to afford (after removal of the volatile material) a light brown oil which amounted to 5.0 g. (83%) of crude 1,1'-[1,4-phenylenebis(methylene)]bispyrrolidone as the free base compound.

The above crude oil (5.0 g.) was then dissolved in 45 benzene and treated with dry hydrogen chloride gas to give an immediate precipitate of the crude hydrochloride salt. Recrystallization of the latter material from methanol then gave analytically pure 1,1'-[1,4-phenylenebis(methylene)]bispyrrolidine dihydrochloride, m.p.>300° C. The yield of pure salt amounted to 4.0 g. (51%).

Anal. Calcd. for $C_{17}H_{26}N_2.2HCl$: C, 60.56; H, 8.26; N, 8.83. Found: C, 60.24; H, 8.24; N, 8.57.

A sample of the pure dihydrochloride salt was then converted back to the free base compound in the same manner as that described in Preparation A to afford a colorless oil, which proved to be pure 1,1'-[1,4-phenylenebis(methylene)]bispyrrolidine as attested to by both mass spectroscopy and nuclear magnetic resonance data.

Preparation G

The procedure described in Preparation A was repeated except that 5.0 g. (0.0189 mole) of α,α-dibromo-m-xylene and 30 g. (0.345 mole) of morpholine were reacted in the absence of a solvent (other than excess morpholine) to afford a crude yellow oil, which amounted to 5.0 g. (96%) of impure 4,4'-[1,3-phenylenebis(methylene)]bismorpholine as the free base compound.

The crude oil (5.0 g.) was then dissolved in 150 ml. of diethyl ether and added slowly to a filtered solution of maleic acid (8.0 g., 0.0689 mole) dissolved in 500 ml. of diethyl ether. A finely-divided white precipitate soon formed and this was quickly recovered as soon as the supernatant liquid was removed from the mixture by means of decantation. The crude dimaleate salt thus obtained was then recrystallized from isopropyl alcohol to afford analytically pure 4,4'-[1,3-phenylenebis(methylene)]bismorpholine dimaleate, m.p. 160°-161° C. The yield of pure salt amounted to 6.0 g. (63%).

Anal. Calcd. for $C_{16}H_{24}N_2O_2.2C_4H_4O_4$: C, 56.69; H, 6.34; N, 5.51. Found: C, 56.81; H, 6.24; N, 5.77.

A sample of the pure dimaleate salt was then converted back to the free base compound in the same manner as that described in Preparation A to afford a colorless oil, which proved to be pure 4,4'-[1,3-phenylenebis(methylene)]bismorpholine as attested to by mass spectroscopy, infrared absorption spectra and nuclear magnetic resonance data.

Preparation H

The procedure described in Preparation A was repeated except that 8.0 g. (0.0408 mole) of α-bromo-o-tolunitrile and 22.0 g. (0.222 mole) of hexamethyleneimine (25 ml.) were reacted in the absence of a solvent (other than excess hexamethyleneimine) by heating the reaction mixture in a dry 100 ml. similarly-equipped reaction flask at the reflux point for a period of 18 hours. In this manner, there was obtained a 7.8 g. (89%) yield of crude 1-(2-cyanophenylmethyl)hexamethyleneimine in the form of a residual oil.

The above crude product (7.8 g.) was then purified in the form of the monomaleate salt by diluting the nitrile-amine with diethyl ether (150 ml.) and then adding same to a filtered solution of maleic acid (6.5 g., 0.056 mole) dissolved in diethyl ether (400 ml.) to afford a crystalline precipitate, which was subsequently recovered after removal of the supernatant liquid by means of decantation. Recrystallization of the crystalline solid material from isopropyl alcohol then gave analytically pure 1-(2-cyanophenylmethyl)hexamethyleneimine monomaleate, m.p. 113°-115° C. The yield of pure salt amounted to 9.0 g. (67%).

Anal. Calcd. for $C_{14}H_{18}N_2.C_4H_4O_4.C$, 65.44; H, 6.71; N, 8.48. Found: C, 65.59; H, 6.76; N, 8.48.

A sample of the above pure maleate salt (4.5 g., 0.013 mole) was then converted back to the corresponding free base compound in the same manner as that described in Preparation A to afford a colorless oil, which proved to be pure 1-(2-cyanophenylmethyl)hexamethyleneimine as attested to by mass spectroscopy, infrared absorption spectra and nuclear magnetic resonance data. This oil was then dissolved in 280 ml. of diethyl ether, to which there was subsequently added in small separate portions 3.0 g. (0.0791 mole) of lithium aluminum hydride. After stirring the resulting gray suspension for a period of 48 hours while at room temperature, the excess hydride reagent was thereafter destroyed by the cautious addition of 4 N aqueous potassium hydroxide thereto. The treated aqueous mixture so obtained was then carefully extracted with three-50 ml. portions of diethyl ether, and the ethereal extracts were subsequently combined and dried over anhydrous magnesium sulfate. After removal of the drying agent by means of filtration and the solvent by means of evaporation under reduced pressure, there was obtained a 1.8 g. (51%) yield of crude 1-(2-aminomethylphenylmethyl)-hexamethyleneimine as the residual material.

The crude diamine base (1.8 g.) was then converted to the corresponding dimaleate salt by dissolution in diethyl ether (100 ml.) and then adding same to a filtered solution of maleic acid (5.0 g., 0.043 mole) dissolved in diethyl ether (300 ml.) to afford a crystalline precipitate. The supernatant ether liquid was then removed from the solid material by means of decantation and the product was subsequently recrystallized from isopropyl alcohol to give analytically pure 1-(2-aminomethylphenylmethyl)hexamethyleneimine dimaleate, m.p. 122°–124° C. The yield of pure salt amounted to 1.4 g. (23%).

Anal. Calcd. for $C_{14}H_{22}N_2.2C_4H_4O_4$: C, 58.66; H, 6.71; N, 6.22. Found: C, 58.36; H, 6.71; N, 6.14.

A sample of the pure dimaleate salt was then reconverted back to the free base compound in the same manner as that described in Preparation A to afford a colorless oil, which proved to be pure 1-(2-aminomethylphenylmethyl)hexamethyleneimine as attested to by both mass spectroscopy and nuclear magnetic resonance data.

Preparation I

To a 25 ml. solution of 4 N aqueous sodium hydroxide contained in a separatory funnel, there were added 2.103 g. (0.00416 mole) of 1,1-[1,2-phenylenebis(methylene)]bispiperidine dimaleate (the product of Preparation A). The resulting milky suspension was next extracted with chloroform and the organic layer was dried over anhydrous magnesium sulfate, filtered and subsequently concentrated in vacuo to afford a colorless oil. The latter oil was then taken up in a mixture benzene (100 ml.) and methylene chloride (15 ml.), to which there were subsequently added 47.9 g. (0.337 mole) of iodomethane (21 ml.). After standing overnight (~16 hours) at room temperature (~25° C.), the crude reaction mixture was refluxed on a steam bath and then cooled, once again, to room temperature. The supernatant liquid was then decanted from the mixture, and the resulting tan solid material was subsequently triturated with fresh n-hexane to afford 1.94 g. (84%) of crude dimethiodide salt. Recrystallization of the latter material from aqueous ethanol then gave analytically pure 1,1'-dimethyl-1,1'-[1,2-phenylenebis(methylene)]-bispiperidinium diiodide, m.p. 240°–242° C. (decomp.). The yield of pure quaternary salt amounted to 1.46 g. (63%).

Anal. Calcd. for $C_{18}H_{28}N_2.2CH_3I$: C, 43.17; H, 6.16; N, 5.03. Found: C, 43.05; H, 5.92; N, 5.12.

Preparation J

In a dry 250 ml. round-bottomed reaction flask equipped with magnetic stirrer, oil bath, reflux condenser and nitrogen-inlet tube, there were placed 5.0 g. (0.291 mole) of trans-1,2-cyclohexanedicarboxylic acid and 40.8 g. (0.342 mole) of thionyl chloride (25 ml.). The resulting suspension was then heated at the reflux point for a period of four hours and finally cooled to room temperature (~25° C.). After removal of the volatile liquids by first concentrating the spent reaction mixture under reduced pressure, there was obtained crude trans-1,2-cyclohexanedicarboxylic acid chloride as the residual material.

The above acid chloride was next dissolved in methylene chloride (100 ml.) and the resulting solution was cooled in an ice bath (with stirring), while the contents of an addition funnel containing 21.5 g. (0.253 mole) of piperidine (25 ml.) in 100 ml. of methylene chloride were slowly added thereto in a dropwise fashion with constant agitation being maintained throughout the entire addition step (this required approximately three hours). The cloudy reaction mixture so obtained was then stirred at room temperature overnight (~16 hours) and finally diluted with chloroform. The resulting organic solution was then washed successively with two-50 ml. portions of 3 N hydrochloric acid, two-25 ml. portions of saturated aqueous sodium bicarbonate and one-25 ml. portion of saturated brine (NaCl). After drying the organic solution over anhydrous magnesium sulfate and filtering, followed by removal of the solvent via evaporation under reduced pressure, there was obtained 10.5 g. of crude diamide in the form of a pale yellow oil which gradually solidified on standing.

The above diamide (10.5 g.) was then placed in a 1-liter round-bottomed reaction flask equipped with magnetic stirrer, reflux condenser and nitrogen-inlet tube, and also containing 8.09 (0.211 mole) of lithium aluminum hydride suspended in 300 ml. of dry tetrahydrofuran (the tetrahydrofuran had previously been freshly distilled over lithium aluminum hydride and then stored over molecular sieves). The resulting gray suspension was then heated at the reflux point for a period three days (~72 hours) and finally cooled to 0° C. with the aid of an ice-bath. The spent reaction mixture was then carefully treated with 4 N aqueous potassium hydroxide in order to completely destroy excess hydride reagent, followed by stirring at room temperature for a period of one hour in order to granulate the resulting solids, which were thereafter removed by means of filtration. The treated aqueous mixture so obtained was then thoroughly extracted with diethyl ether, and the separated ether layers subsequently combined and dried over anhydrous magnesium sulfate. After removal of the drying agent by means of filtration and the solvent by means of evaporation under reduced pressure, there was obtained a pale yellow oil consisting of crude diamine base as the residual material.

The crude diamine base was then converted to the corresponding dihydrochloride salt by dissolution in diethyl ether (200 ml.), followed by extraction of the latter solution with 6 N aqueous hydrochloric acid. The combined acidified aqueous layers were then basified and the resulting organic base re-extracted into chloroform, followed by drying over anhydrous magnesium sulfate and filtering to give a clear chloroform solution that was subsequently concentrated in vacuo to afford a pale yellow oil. In this manner, there were ultimately obtained 5.2 g. (64%) of pure 1,1'-[trans-1,2-cyclohexylenebis(methylene)]bispiperidine as the free base. Further purification was then achieved by means of column chromatography, using 500 ml. of silica gel (EM-60, available from E. Merck, A. G. of Darmstadt, West Germany) and then eluting with an ethyl acetate/benzene/diethylamine (20:20:1 by volume) mixture by taking 100 ml. fractions. The pure diamine base was isolated in fraction Nos. 4–7 and these were subsequently combined, dissolved in diethyl ether (50 ml.) and treated with dry hydrogen chloride gas until saturation of same with respect to said gas was complete. The crude oil which soon separated was then triturated with isopropyl alcohol to yield a crystalline solid. Recrystallization of the latter material from isopropyl alcohol/diethyl ether and then from acetonitrile/diethyl ether finally gave analytically pure 1,1'-[trans-1,2-cyclohexylenebis(methylene)]bispiperidine dihydrochloride, m.p. 265°-267° C. The yield of pure salt amounted to 1.4 g. (14%).

Anal. Calcd. for $C_{18}H_{34}N_2.2HCL$: C, 61.52; H, 10.32; N, 7.97. Found: C, 61.46; H, 10.43; N, 7.95.

A sample of the pure dihydrochloride salt was then reconverted back to the free base compound in the same manner as that described in Preparation A to afford a clear viscous oil, which proved to be pure 1,1'-[trans-1,2-cyclohexylenebis(methylene)]bispiperidine as attested by both mass spectroscopy and nuclear magnetic resonance data.

Preparation K

The procedure described in Preparation J was essentially followed to prepare trans-3,6-endomethylene-1,2,3,6-tetrahydrophthalonamide [*Chemical Abstracts*, Vol. 58, p. 3331D (1964)], except that 13.5 g. (0.062 mole) of trans-3,6-endomethylene-1,2,3,6-tetrahydrophthaloyl chloride and 21.5 g (0.253 mole) of piperidine (25 ml.) were reacted in 200 ml. of benzene, and the entire reaction mixture was stirred for 24 hours at room temperature (~25° C.) after the initial exothermic reaction had subsided. In this manner, there was ultimately obtained an 18.6 g. (95%) yield of crude diamide (m.p. 144°-150° C.), which was used as such in the next reaction step without any further purification being necessary [A sample was recrystallized from ethyl acetate/n-hexane to give analytically pure material, m.p. 159°-160° C. (identical with the literature value)].

The above diamide (5.0 g., 0.0259 mole) was then cautiously placed in a dry 500 ml. round-bottomed reaction flasked equipped with magnetic stirrer, reflux condenser and nitrogen-inlet tube, and also containing 8.0 g. (0.211 mole) of lithium aluminum hydride suspended in 150 ml. of dry tetrahydrofuran. The resulting gray suspension was then heated at the reflux point for a period of 48 hours and finally cooled to room temperature. The spent reaction mixture was thereafter worked-up in exactly the same manner as the corresponding mixture in Preparation J to afford a pale yellow oil, which amounted to 4.9 g. (66%) of crude diamine base as the residual material.

The above crude diamine (4.9 g.) was then dissolved in methylene chloride and extracted into cold 6 N aqueous hydrochloric acid, followed by basification of the combined aqueous layers (with cooling) and re-extraction into methylene chloride as before. After drying over magnesium sulfate and filtering, there was obtained a clear solution that was subsequently concentrated in vacuo to afford 2.9 g. of a colorless oil. The latter material (which proved to be a 39% yield of pure diamine) was then dissolved in diethyl ether (100 ml.) and filtered, and the filtered solution subsequently treated with 7.0 g. (0.0603 mole) of maleic acid in 500 ml. of diethyl ether (also a filtered solution) to yield a white-oily wax. Decantation of the supernatant liquid and two recrystallization from isopropyl alcohol then gave analytically pure 1,1'-[5-norbornen-trans-2,3-ylenebis(methylene)]bispiperidine dimaleate, m.p. 137°-138° C. The yield of pure salt amounted to 4.2 g. (31%).

Anal. Calcd. for $C_{19}H_{32}N_2.2C_4H_4O_4$: C, 62.29; H, 7.74; N, 5.38. Found: C, 61.98; H, 7.83; N, 5.31.

A sample of the pure dimaleate salt was then converted back to the free base compound by dissolution in water and treatment in the same manner as that described for the corresponding salt in Preparation A to afford a colorless viscous oil, which proved to be pure 1,1'-[5-norbornen-trans-2,3-ylenebis(methylene)]bispiperidine as attested to by both mass spectroscopy and nuclear magnetic resonance data.

Preparation L

To a 1-liter Erlenmeyer flask equipped with a magnetic stirrer, there were added 100 ml. of a 25% aqueous solution of dimethylamine (0.555 mole) followed by the slow cautious addition of 25.4 g. (0.125 mole) of phthaloyl chloride (18 ml.) thereto with constant agitation being maintained throughout the entire addition step. The reaction mixture was then stirred at room temperature (~25° C.) for a period of 18 hours, diluted with methylene chloride, washed with saturated aqueous sodium bicarbonate solution and dried over anhydrous magnesium sulfate. After removal of the drying agent by means of filtration and the solvent by means of evaporation under reduced pressure, there was obtained a 26 g. (94.5%) yield of the diamide in a highly crystalline form. Two recrystallizations of the latter material from ethyl acetate/n-hexane then gave analytically pure N,N,N',N'-tetratetramethylphthaloamide, m.p. 118°-120° C.

Anal. Calcd. for $C_{12}H_{16}N_2O_2$: C, 65.43; H, 7.32; N, 12.72. Found: C, 65.18; H, 7.34; N, 12.53.

The recrystallized diamide (4.0 g., 0.0182 mole) was then placed in a 500 ml. round-bottomed reaction flask equipped with a magnetic stirrer, reflux condenser and nitrogen-inlet tube, and also containing 5.0 g. (0.132 mole) of lithium aluminum hydride suspended in 175 ml. of dry tetrahydrofuran. The resulting gray suspension was then heated at the reflux point for a period of 72 hours and finally cooled to room temperature. The spent reaction mixture was thereafter worked-up in exactly the same manner as that previously described for the corresponding mixture in Preparation J and there was ultimately obtained a 3.4 g. (97%) yield of the desired diamine (as the free base) in the form of a pale yellow oil.

A portion of the above diamine oil (2.8 g.) was then dissolved in diethyl ether (100 ml.) and slowly poured into a filtered solution contaning 3.5 g. (0.0302 mole) of maleic acid dissolved in diethyl ether (200 ml.). A white gummy solid soon formed. This material was later triturated with diethyl ether several times and thereafter recrystallized from isopropyl alcohol to afford analytically pure [1,2-phenylenebis(methyl)]bis(dimethylamine) dimaleate, m.p. 114°-116° C. The yield of pure salt amounted to 275 g. (36%).

Anal. Calcd. for $C_{12}H_{20}N_2.2C_4H_4O_4$: C, 56.59; H, 6.64; N, 6.60. Found: C, 56.49; H, 6.57; N, 6.32.

A sample of the pure dimaleate salt was then converted back to the free base compound by dissolution in water and treatment in the same manner as that described for the corresponding salt in Preparation A to afford a colorless oil, which proved to be pure [1,2-phenylenebis(methylene)]bis(dimethylamine) as attested to by both mass spectroscopy and nuclear magnetic resonance data.

Preparation M

A suspension consisting of 1.80 g. (0.00902 mole) of 2,3-dihydro-2-(2-carboxyphenylmethyl)-1H-isoindole as the acid chloride [J. Bornstein et al., *Journal of the American Chemical Society*, Vol. 78, p. 83 (1956)] and 1.08 g. (0.0124 mole) of dry morpholine contained in a 50 ml. round-bottomed reaction flask equipped with reflux condenser, drying tube and magnetic stirrer was heated under reflux for a period of 18 hours to afford a yellow brown solution. The latter was then diluted with ethyl acetate (400 ml.) and washed well with three-25 ml. portions of water, two-25 ml. portions of saturated aqueous sodium bicarbonate and two-25 ml. portions of water in that order. After drying over magnesium sulfate and filtering, followed by removal of the solvent from the resulting filtrate via evaporation under reduced pressure, there was obtained a white crystalline solid. Recrystallization of the latter material from ethyl acetate/n-hexane then gave analytically pure 2,3-dihydro-2-[2-(4-morpholinocarbonyl)phenylmethyl]-1H-isoindole, m.p. 141.5°-142.5° C. The yield of pure amide product amounted to 1.87 g. (59%).

Anal. Calcd. for $C_{20}H_{24}N_2O_2$: C, 68.53; H, 5.18; N, 8.00. Found: C, 68.54; H, 5.02; N, 8.40.

The above phthalimido-morpholine amide (4.0 g., 0.0114 mole) was then placed in a dry 500 ml. round-bottomed reaction flask with magnetic stirrer, reflux condenser and drying tube, and also containing 5.0 g. (0.132 mole) of lithium aluminum hydride suspended in 200 ml. of dry tetrahydrofuran. The resulting gray suspension was then heated at the reflux point for a period of 72 hours and finally cooled to room temperature. The spent reaction mixture was thereafter worked-up in exactly the same manner as the corresponding mixture in Preparation J to ultimately afford a yellow brown oil, which proved to be crude 2,3-dihydro-2-[2-(4-morpholinomethyl)phenylmethyl]-1H-isoindole.

The crude diamine oil so obtained as the above free base compound was then taken up in chloroform and extracted into 3 N aqueous hydrochloric acid, followed by basification of the combined aqueous layers in the cold and re-extraction into chloroform once again. After drying over magnesium sulfate and filtering, there was obtained a clear solution that was subsequently concentrated in vacuo to afford the purified diamine in the form of a residual oil. The latter material was then diluted with diethyl ether (100 ml.) and filtered, and the filtered solution subsequently added to a filtered solution of maleic acid (5.0 g, 0.043 mole) in diethyl ether (200 ml.) to yield a crude precipitate as product. Recrystallization of the precipitate from isopropyl alcohol (three times) then gave analytically pure 2,3-dihydro-2-[2-(4-morpholinomethyl)phenylmethyl]-1H-isoindole dimaleate, m.p. 121°-122° C. The yield of pure salt amounted to 820 mg. (13%).

Anal. Calcd. for $C_{20}H_{26}N_2O.2C_4H_4O_4$: C, 62.21; H, 5.97; N, 5.18. Found: C, 62.34; H, 6.11; N, 5.21.

A sample of the pure dimaleate salt was then converted back to the free base compound by dissolution in water and treatment in the same manner as that described for the corresponding salt in Preparation A to afford a colorless oil, which proved to be pure 2,3-dihydro-2-[2-(4-morpholinomethyl)phenylmethyl]-1H-isoindole as evidenced by nuclear magnetic resonance data.

Preparation N

The procedure described in Preparation M was repeated except that 1.68 g. (0.00561 mole) of 2,3-dihydro-2-(2-carboxyphenylmethyl)-1H-isoindole as the acid chloride [J. Bornstein et. al., *Journal of the American Chemical Society*, Vol. 78, p. 83 (1956)] and 1.12 g. (0.132 mole) of piperidine were reacted in 30 ml. of dry toluene to afford 1.20 g. (61%) pure 2,3-dihydro-2-[2-(1-piperidinocarbonyl)phenylmethyl]-1H-isoindole, m.p. 100.5°-101.5° C. after recrystallization from ethyl acetate/n-hexane.

Anal. Calcd. for $C_{21}H_{24}N_2O$: C, 72.40; H, 5.79; N, 8.04. Found: C, 72.07; H, 5.71; N, 7.91.

The above phthalimido-piperidino amide (0.50 g., 0.00143 mole) was then placed in a suitable round-bottomed reaction flask equipped with magnetic stirrer, reflux condenser and drying tube, and also containing 1.0 g. (0.0264 mole) of lithium aluminum hydride suspended in 300 ml. of dry tetrahydrofuran. The resulting gray suspension was then heated at the reflux point for a period of 72 hours and finally cooled to room temperature. The spent reaction mixture was thereafter worked-up in exactly the same manner as the corresponding mixture in Preparation J to ultimately afford a lavender-colored viscous oil, which amounted to 0.43 g. (98%) of crude 2,3-dihydro-2-[2-(1-piperidinomethyl)-phenylmethyl]-1H-isoindole as the residual base.

The above crude diamine base compound (1.63 g., 0.0053 mole) was then converted to the corresponding monomaleate salt in the usual manner, using 0.63 g. (0.0054 mole) of maleic acid as reagent. The salt product so obtained was then recrystallized twice from isopropyl alcohol to give analytically pure 2,3-dihydro-[2-(1-piperidinomethyl)phenylmethyl]-1H-isoindole monomaleate, m.p. 165.5°-166.5° C. The yield of pure salt amounted to 720 mg. (33%).

Anal. Calcd. for $C_{21}H_{26}N_2.C_4H_4O_4$: C, 71.07; H, 7.16, N, 6.63. Found: C, 71.29; H, 7.22; N, 6.56.

Preparation O

In a dry 500 ml. round-bottomed reaction flask equipped with a magnetic stirrer, reflux condenser and nitrogen-inlet tube, there were placed 10 g. (0.0628 mole) of 3,4-furandicarboxylic acid and 32.6 g. (0.274 mole) of thionyl chloride (20 ml.) in 100 ml. of benzene. The resulting solution was then heated at the reflux point for a period of three hours and finally cooled to room temperature (~25° C.). After removal of the volatile liquid via concentration under reduced pressure, there was obtained crude 3,4-furandicarboxylic acid chloride as the residual material.

The above acid chloride was then cautiously treated with a solution of piperidine (25.8 g., 0.303 mole) in chloroform (100 ml.), and the resulting mixture stirred at room temperature for 18 hours. At this point, the spent reaction mixture was diluted with ethyl acetate (500 ml.) and thereafter washed successively with three-50 ml. portions of 3 N hydrochloric acid, three-50 ml. portions of saturated aqueous sodium bicarbonate and three-50 ml. portions of saturated brine. The organic solution was then dried over anhydrous magnesium sulfate and filtered, and the resulting clear filtrate was subsequently evaporated under reduced pressure to yield 14.5 g. (80%) of the corresponding diamide in the form of a crystalline solid residue. Recrystallization of the latter material from ethyl acetate/n-hexane then gave analytically pure 1,1'-[3,4-furandiylbis(carbonyl)]bispiperidine, m.p. 180°-183° C.

Anal. Calcd. for $C_{16}H_{22}N_2O_3$: C, 66.19; H, 7.64; N, 9.65. Found: C, 66.04; H, 7.58; N, 9.60.

The above diamide (5.0 g., 0.0172 mole) was then placed in a suitable round-bottomed reaction flask equipped with magnetic stirrer, reflux condenser and drying tube, and also containing 8.0 g. (0.211 mole) of lithium aluminum suspended hydride in 150 ml. of dry tetrahydrofuran. The resulting suspension was then refluxed for 72 hours and finally cooled to room temperature. The spent reaction mixture was thereafter worked up in exactly the same way as the corresponding mixture in Preparation J to afford crude 1,1'-[3,4-furandiylbis(methylene)]bispiperidine in a 4.5 g. (100%) yield.

The above crude diamine base (4.5 g.) was then dissolved in diethyl ether and treated with dry hydrogen chloride gas to give an immediate precipitate of the crude dihydrochloride salt. Recrystallization of the latter material twice from isopropyl alcohol then gave analytically pure 1,1'-[3,4-furandiylbis(methylene)]bispiperidine dihydrochloride (as a hydrated salt), m.p. 145°–147° C.

Anal. Calc. for $C_{16}H_{26}N_2O.2HCl.0.25H_2O$: C, 56.55; H, 8.45 N, 8.24 Found: C, 56.82; H, 8.82; N, 8.28.

Preparation P

The procedure described in Preparation O was essentially followed to prepare 1,1'-[3,4-furandiylbis(carbonyl)]bispyrrolidine, except that pyrrolidine was the reagent of choice employed instead of piperidine (using the same molar proportions as before). In this particular case, the corresponding diamide obtained was initially isolated as a crude residue (m.p. 137°–145° C.) in a 13.6 g. (83%) yield. Recrystallization of the latter material from ethanol/n-hexane then gave 11.8 g. (72%) of pure product melting at 142°–144° C.

The above diamide (3.0 g., 0.0114 mole) was then placed in a suitable round-bottomed reaction flask equipped with magnetic stirrer, reflux condenser and drying tube, and also containing 3.0 g. (0.0791 mole) of lithium aluminum hydride suspended in 150 ml. of dry tetrahydrofuran. The resulting suspension was then heated at the reflux point for a period of 72 hours and finally cooled to room temperature. The spent reaction mixture was thereafter worked-up in exactly the same manner as the corresponding mixture in Preparation J to afford crude 1,1'-[3,4-furandiylbis(methylene)[bispyrrolidine in a 2.0 g. (82%) yield.

The above crude diamine base (2.0 g.) was then converted to the corresponding dimaleate salt in the usual way, using a slight excess (2.2 g.) of maleic acid for these purposes. The salt product so obtained was then recrystallized twice from methanol/diethyl ether to give analytically pure 1,1'-[3,4-furandiylbis(methylene)]bispyrrolidine dimaleate, m.p. 125°–127° C. The yield of pure salt amounted to 1.25 g. (24%).

Anal. Calcd. for $C_{14}H_{22}N_2O.2C_4H_4O_4$: C, 56.65; H, 6.48; N, 6.01. Found: C, 56.78; H, 6.47; N, 5.74.

A sample of the pure dimaleate salt was then converted back to the free base compound by dissolution in water and treatment in the same manner as that described for the corresponding salt in Preparation A to afford a colorless viscous oil, which proved to be pure 1,1'-[3,4-furandiylbis(methylene)]bispyrrolidine as attested to by nuclear magnetic resonance data.

EXAMPLE I

In a 500 ml. round-bottomed reaction flask equipped with magnetic stirrer, reflux condenser and nitrogen-inlet tube, there were placed 10 g. (0.032 mole) of crude 4-nitro-α,α'-dibromo-o-xylene [M. Kerfanto, *Bulletin de la Société Chimique de France*, Vol. 12, p. 3537 (1965)] and 44.8 g. (0.526 mole) of piperidine (52 ml.) all dissolved in 100 ml. of benzene. The resulting mixture was then heated at the reflux point for a period of 18 hours and finally cooled to room temperature (~25° C.). The spent reaction mixture was then diluted with 500 ml. of benzene and thereafter washed with four-100 ml. portions of water, followed by drying over anhydrous magnesium sulfate. After removal of the drying agent by means of filtration and the solvent by means of evaporation under reduced pressure, there was obtained a 59% yield of crude 1,1'-[4-nitro-1,2-phenylenebis(methylene)]bispiperidine as a residue in the form of a yellow oil.

The above crude oil (6.0 g.) was then dissolved in methylene chloride and extracted with 6 N aqueous hydrochloric acid. The acidified aqueous layer was thereafter basified with 6 N aqueous potassium hydroxide, keeping the temperature below 30° C. with the aid of an ice bath, and the resulting organic base re-extracted with methylene chloride, followed by drying of the organic extract over anhydrous magnesium sulfate in same manner as before. After removal of the drying agent by means of filtration and the solvent by means of evaporation under reduced pressure, there were ultimately obtained 3.0 g. (29%) of partially purified 1,1-[4-nitro-1,2-phenylenebis(methylene)]bispiperidine as the free base compound in the form of a colorless oil. Conversion to the dihydrochloride salt was then accomplished by dissolving said diamine in diethyl ether (100 ml.), followed by filtering to remove a trace of insolubles and thereafter saturating the filtered solution with anhydrous hydrogen chloride. The precipitated salt was then recovered by means of filtration and the hygroscopic solid recrystallized twice from isopropyl alcohol to afford analytically pure 1,1'-[4-nitro-1,2-phenylenebis(methylene)]bispiperidine dihydrochloride monohydrate, m.p. 248°–250° C. (decomp.). The yield of pure salt amounted to 1.5 g. (11.5%).

Anal. Calcd. for $C_{18}H_{27}N_3O_2.2HCl.H_2O$: C, 52.94; H, 7.65; N, 10.28. Found: C, 53.16; H, 7.23; N, 10.18.

A sample of the pure dihydrochloride salt (as the monohydrate) was then reconverted back to the free base compound by dissolution in water and treatment in the same manner as that earlier described for the salt in Preparation A to afford a colorless oil, which proved to be pure 1,1'-[4-nitro-1,2-phenylenebis(methylene)bispiperidine as attested to by both mass spectroscopy and nuclear magnetic resonance data.

EXAMPLE II

A suspension consisting of 10 g. (0.0762 mole) of 3,4-dimethylbenzonitrile, 29.9 g. (0.1677 mole) of N-bromosuccinimide and 0.25 g. of benzoyl peroxide in carbon tetrachloride, all contained in a 1-liter round-bottomed reaction flask equipped with nitrogen-inlet tube and reflux condenser, was heated at the reflux point for a period of 21 hours while being illuminated with a medium wave length U.V. (ultraviolet) lamp. The reaction mixture was then cooled to room temperature (~25° C.), next filtered to remove floating solids and thereafter stripped of volatile liquids by means of evaporation under reduced pressure to afford 24 g. of a crude brown oil as the residue, which proved to be impure 4-cyano-α,α'-dibromo-o-xylene.

The above crude oil (24 g.), consisting of the impure dibromo compound, was next treated (without any further purification) with 40 ml. (0.404 mole) of piperidine by first dissolving the oil in 250 ml. of benzene and then adding the piperidine thereto. After an initially mild exothermic reaction, the resulting mixture was heated at the reflux point for a period of 72 hours and finally cooled to room temperature. The spent reaction mixture was then washed with six-100 ml. portions of water and dried over anhydrous magnesium sulfate prior to being filtered, followed by treatment of the resulting filtrate with activated carbon in a conventional manner in order to effect still further purification. The purified solution was then concentrated under reduced pressure and there were ultimately obtained 14.8 g. of a dark brown oil, which proved to be impure 1,1'-[4-cyano-1,2-phenylenebis(methylene)]bispiperidine.

The above crude oil (14.8 g.) was then taken up in methylene chloride and the diamine extracted with cold 3 N aqueous hydrochloric acid. The combined acidified aqueous layers were then basified and the resulting organic base back extracted into methylene chloride, followed by drying over anhydrous magnesium sulfate and filtering to give a clear solution that was subsequently concentrated in vacuo to afford a dark brown oil. The latter material amounted to 10.5 g. of purified 1,1'-[4-cyano-1,2-phenylenebis(methylene)]bispiperidine. Further purification was then achieved by means of column chromatography over silica gel, using 600 ml. of silica gel 60 (available from Brinkmann Instruments, Inc. of Westbury, N.Y.) and then eluting with an ethyl acetate/benzene/diethylamine (50:50:0.5 by volume) mixture by taking 100 ml. fractions. The pure diamine was isolated in fraction Nos. 8–14, which were later combined and evaporated to yield a residual oil. The latter substance was then dissolved in diethyl ether, filtered and the ethereal filtrate subsequently treated with anhydrous hydrogen chloride to afford a yellow solid as precipitate. Recrystallization of the recovered material (which is extremely hydgroscopic) three times from methanol/diethyl ether then gave analytically pure 1,1'-[4-cyano-1,2-phenylenebis(methylene)]bispiperidine dihydrochloride (as a partial hydrate) in the form of pale yellow crystals melting at 268°–270° C. The yield of pure salt amounted to 1.8 g. (4%).

Anal. Calcd. for $C_{19}H_{27}N_3 \cdot 2HCl \cdot 0.125H_2O$: C, 61.24; H, 7.91; N, 11.27. Found: C, 61.19; H, 7.89; N, 11.18.

A sample of the pure dihydrochloride salt was then reconverted back to the free base compound by dissolution in water and treatment in essentially the same manner as that described earlier for the salt in Preparation A (except that 4 N aqueous KOH was used instead of 3 N KOH in this particular instance) to afford a highly viscous oil, which proved to be pure 1,1'-[4-cyano-1,2-phenylenebis(methylene]bispiperidine as attested to by mass spectroscopy, infrared absorption spectra and nuclear magnetic resonance data.

EXAMPLE III

A solution consisting of 5.9 g. (0.0499 mole) of indan (available from the Aldrich Chemical Company, Inc., Milwaukee, Wis.), 17.8 g. (0.100 mole) of N-bromosuccinimide and 0.15 g. (0.00062 mole) of benzoyl peroxide dissolved in carbon tetrachloride was placed in a 2-liter, one-necked, round-bottomed reaction flask equipped with magnetic stirrer, reflux condenser and nitrogen-inlet tube. The solution was then heated at the reflux point while under a nitrogen atmosphere, in addition to being constantly irradiated with a standard sunlamp throughout the heating period which required approximately three hours. At the end of this time, the reaction mixture was cooled to room temperature ($\sim 25°$ C.) and filtered, and the resulting brown to amber-colored filtrate containing the crude dibromo derivative was saved for the next reaction step without any further purification being necessary.

The above filtrate was then treated with 50 ml. (0.506 mole) of piperidine, which was added in a dropwise manner over a one-hour period while still keeping the reaction mixture at room temperature. The resulting suspension was then heated at the reflux point for a period of four hours and finally cooled to room temperature prior to being extracted with five-200 ml. portions of 2 N aqueous hydrochloric acid. The combined aqueous acidified layers were next back-extracted with one-50 ml. portion of carbon tetrachloride and the separated aqueous layer was thereafter carefully basified with 3 N aqueous potassium hydroxide, while using an ice bath for cooling purposes. Extraction of the latter basified medium with chloroform (four-200 ml. portions were used), followed by drying over anhydrous magnesium sulfate and filtering then gave a clear solution that was subsequently concentrated in vacuo to afford crude diamine base as a semisolid brown residual material. This substance proved to be impure indan-1,3-diyl-bis(1,1'-piperidine) in the form of a cis/trans mixture.

The above crude product was then taken up in few ml. of chloroform and placed on a silica gel chromatography column, using 250 ml. of silica gel of 70–230 mesh size. Elution was then accomplished with 150 ml. of n-hexane, followed by the use of a n-hexane/triethylamine (9:1 by volume) mixture and thereafter taking 30 ml. fractions of the latter. Examination via thin layer chromatography (TLC), using silica gel plates and a n-hexane/triethylamine (9:1 by volume) solvent system, as well as by nuclear magnetic resonance (nmr) spectral studies, then revealed that the stereoisomeric amines had been separated into the pure cis- and trans-isomers in fraction Nos. 2 and 4, respectively, while a mixture of same was obtained in fraction No. 3. The aforesaid stereochemistry was assigned on the basis of the expected polarity of the cis- and trans-isomers on chromatography studies, as well as on the observed symmetry of the nuclear magnetic resonance (nmr) spectra.

Fraction No. 2, which amounted to a 19.6% overall yield, was then triturated with isopropyl alcohol to afford analytically pure cis-indan-1,3-diyl-bis(1,1'-piperidine), m.p. 114°–115° C.

Anal. Calcd. for $C_{19}H_{28}N_2$: C, 80.23; H, 9.92; N, 9.85. Found: C, 79.99; H, 10.06; N, 9.86.

Fraction No. 4, which amounted to an 8.4% overall yield, was first converted to its dimaleate salt by treatment with a slight excess of maleic acid in diethyl ether. Recrystallization of the initial precipitate from isopropyl alcohol than gave analytically pure trans-indan-1,3-diylbis(1,1'-piperidine)dimaleate, m.p. 160°–161° C.

Anal. Calcd. for $C_{19}H_{28}N_2 \cdot 2C_4H_4O_4$: C, 62.77; H, 7.03; N, 5.42. Found: C, 72.78; H, 6.94; N, 5.44.

A sample of the pure dimaleate salt was then converted back to the free base compound by dissolution in water and treatment in the same manner as that described for the corresponding salt in Preparation A to afford a colorless oil, which proved to be pure trans-indan-1,3-diyl-bis(1,1'-piperidine) as attested to by thin layer chromatography and nuclear magnetic resonance data (which differed significantly from that of the cis-isomer).

EXAMPLE IV

The procedure described in Preparation M was repeated except that 2.0 g. (0.0067 mole) of 2,3-dihydro-2-

(2-carboxyphenylmethyl)-1H-isoindole as the acid chloride [J. Borstein et al., *Journal of the American Chemical Society*, Vol. 78, p. 83 (1956)] and 1.44 g. (0.018 mole) of 4-aminopyridine were reacted in 50 ml. of dry toluene to give 1.70 g. (71%) of pure 2,3-dihydro-2-[2-(4-pyridylaminocarbonyl)phenylmethyl]-1H-isoindole, m.p. 215.5°–217.5° C. after recrystallization from ethyl acetate/n-hexane.

Anal. Calcd. for $C_{21}H_{21}N_3O$: C, 70.58; H, 4.23; N, 11.76. Found: C, 70.82; H, 4.35; N, 11.63.

The above phthalimido-pyridylamino amide (1.7 g., 0.000143 mole) was then placed in a suitable round-bottomed reaction flask equipped with magnetic stirrer, reflux condenser and drying tube, and also containing 3.0 g. (0.079 mole) of lithium aluminum hydride suspended in 400 ml. of dry tetrahydrofuran. The resulting gray suspension was then heated at the reflux point for a period of 72 hours and finally cooled to room temperature (~25° C.). The spent reaction mixture was thereafter worked-up in exactly the same manner as the corresponding mixture in Preparation J to ultimately afford an orange oil, which proved to be crude 2,3-dihydro-2-[2-(4-pyridylaminomethyl)phenylmethyl]-1H-isoindole as the residual base.

The above crude triamine base was then converted to the corresponding dimaleate salt in the usual manner, using an excess of maleic acid (as reagent) dissolved in diethyl ether for these purposes. The salt product so obtained was then recrystallized twice from isopropyl alcohol to give analytically pure 2,3-dihydro-2-[2-(4-pyridylaminomethyl)phenylmethyl]-1H-isoindole dimaleate, m.p. 163°–165° C. (decomp.). The yield of pure salt amounted to 800 mg. (31%).

Anal. Calcd. for $C_{21}H_{23}N_3 \cdot 2C_4H_4O_4$: C, 63.60; H, 5.34; N, 7.67. Found: C, 63.20; H, 5.34; N, 7.36.

EXAMPLE V

In a dry 50 ml. round-bottomed reaction flask equipped with magnetic stirrer, oil bath, reflux condenser and nitrogen-inlet tube, there were placed 2.0 g. (0.0102 mole) of 4-methoxyphthalic acid [H. King, *Journal of the Chemical Society*, p. 1157 (1939)] and 7.2 g. (0.0345 mole) of phosphorus pentachloride. The crude solid mixture was then heated to a gentle reflux for a period of three hours while under a nitrogen atmosphere and finally cooled to room temperature (~25° C.). After removal of the volatile components by concentrating the spent reaction mixture under reduced pressure, there was obtained crude 4-methoxyphthaloyl chloride as the residue in the form of a pale yellow solid.

The above acid chloride was next suspended almost immediately in chloroform (100 ml.) and the resulting mixture was treated with 8.51 g. (0.101 mole) of piperidine (10 ml.) by adding same to the mixture in a dropwise fashion over a period of one hour. The crude reaction mixture so obtained was then stirred at room temperature overnight (~16 hours) and finally diluted with 400 ml. of chloroform. The resulting chloroform solution was then washed with ice-cold 3 N aqueous hydrochloric acid until the wash liquids were acidic, followed by successive washes with two-50 ml. portions of saturated aqueous sodium bicarbonate and one-100 ml. portion of saturated brine (NaCl). After drying the washed organic solution over anhydrous magnesium sulfate and filtering, followed by removal of the solvent via evaporation under reduced pressure, there was obtained ca. 5.0 g. of crude diamine in the form of a pale yellow oil which was used as such in the next reaction step without any further purification being necessary.

The above diamide (ca. 5.0 g.) was then taken up in 200 ml. of anhydrous diethyl ether and placed in a three-necked, round-bottomed reaction flask equipped with magnetic stirrer, reflux condenser and nitrogen-inlet tube, to which 4.0 g. (0.105 mole) of lithium aluminum hydride were thereafter slowly added in small portions. The heterogeneous reaction mixture was then stirred at room temperature for a period of four days (~96 hours). The excess hydride reagent present in the mixture was then carefully destroyed by the cautious addition thereto of 4 ml. of water, 4 ml. of 15% aqueous sodium hydroxide and 12 ml. of water in that sequence. The treated mixture was then stirred thoroughly to granulate the aluminum salts, magnesium sulfate was added thereto and the resulting suspension was filtered. Upon removal of the solvent under reduced pressure, there was obtained a pale yellow oil consisting of 3.0 g. of crude diamine base as the residual material.

The crude diamine base (3.0 g.) was then purified by dissolution in chloroform, followed by extraction of the latter solution with ice-cold 3 N aqueous hydrochloric acid. The combined acidified aqueous layers were then basified (with the aid of ice-cooling) and the resulting organic base back extracted into chloroform, using four-100 ml. portions of the latter solvent. After drying over anhydrous magnesium sulfate and filtering, there was ultimately obtained a clear chloroform solution that was subsequently concentrated in vacuo to afford 2.0 g. of pure 1,1'-[4-methoxy-1,2-phenylenebis(methylene)]bispiperidine as the free base in the form of a pale-colored residual oil. The pure diamine oil (2.0 g.) was then dissolved in diethyl ether (200 ml.) and filtered, and the filtered solution was subsequently added to a filtered solution of maleic acid (10 g.; 0.086 mole) dissolved in diethyl ether (600 ml.) to afford a pale yellow gum as the product. Recrystallization of the latter material twice from isopropyl alcohol/diethyl ether then gave analytically pure 1,1'-[4-methoxy-1,2-phenylenebis(methylene)]bispiperidine dimaleate, m.p. 124°–126° C. The yield of pure salt amounted to 1.99 g. (9.8%).

Anal. Calcd. for $C_{19}H_{30}N_2O \cdot 2C_4H_4O_4$: C, 60.66; H, 7.16; N, 5.24. Found: C, 60.69; H, 7.01; N, 4.89.

A sample (250 mg.) of the pure dimaleate salt was then converted back to the free base compound in the same manner as that described for the corresponding salt in Preparation A (except that 4 N aqueous potassium hydroxide was the reagent employed in this particular instance) to afford a pale viscous oil, which proved to be pure 1,1'-[4-methoxy-1,2-phenylenebis(methylene)]bispiperidine as attested to by mass spectroscopy, infrared absorption spectra and nuclear magnetic resonance data.

EXAMPLE VI

A solution consisting of 10 g. (0.0598) of 2,3-pyridinecarboxylic acid (available from the Aldrich Chemical Company, Inc., Milwaukee, Wis.), 12 ml. (0.164 mole) of thionyl chloride and 0.65 g. (0.009 mole) of N,N-dimethylformamide all dissolved in 10 ml. of toluene was heated at the reflux point for a period of three hours and finally cooled to room temperature (~25° C.). After removal of the volatile liquids by evaporation under reduced pressure, there was obtained crude 2,3-pyridinecarboxylic acid chloride as the residual material.

The above acid chloride was then diluted with 15 ml. of tetrahydrofuran and cautiously added to a chilled solution consisting of 100 ml. (1.011 mole) of piperidine dissolved 100 ml. of 4 N aqueous potassium hydroxide. This was accomplished by adding the acid chloride solution in a dropwise manner over a 30-minute period to the aforesaid piperidine solution (previously cooled to 0° C.), while maintaining a constant and vigorous agitation of the overall reaction mixture throughout the course of the entire addition step. The resulting mixture was then stirred for 24 hours at room temperature and the suspension so obtained was thereafter extracted with four-250 ml. portions of chloroform, followed by drying of the latter organic extracts over anhydrous magnesium sulfate. After removal of the drying agent by means of filtration and the organic solvent by means of evaporation under reduced pressure, there was obtained a residual solid material consisting of pure pyridin-2,3-diyldicarbonylbis(1,1'-piperidine). The yield of pure diamide amount to 6.5 g. (36%).

The above diamide (3.0 g., 0.01 mole) was then taken up in 100 ml. of dry toluene and placed in a 250 ml. three-necked, round bottomed reaction flask equipped with a mechanical stirring apparatus, nitrogen-inlet tube and serum cap. After cooling the contents of the reaction flask to −78° C. with the aid of a dry ice/acetone bath mixture, an excess (5 ml.) of diisobutylaluminum hydride solution was added to the chilled toluene solution via a syringe. The resulting clear mixture was then stirred continuously at −78° C. for a period of three hours. The reaction was then quenched by the careful addition (via a syringe) of 2.5 ml. of glacial acetic acid dissolved in 10 ml. of toluene, and the spent reaction mixture was thereafter combined with 400 ml. of diethyl ether and 150 ml. of saturated aqueous sodium potassium tartrate solution, whereupon a fine copious precipitate soon formed. Filtration of the thoroughly emulsified suspension then gave a filtrate which separated into two layers, and this was followed by washing the separated ether layer with water and drying same over anhydrous magnesium sulfate. After removal of the drying agent by means of filtration and the solvent by means of evaporation under reduced pressure, there was ultimately obtained crude pyridin-2,3-diyl-dimethylenebis(1,1'-piperidine) in the form of a brown oily residue.

The above crude product was then chromatographed over silica gel, using 25 g. of said siliceous material of 70-230 mesh size and eluting with 25 ml. fractions of ethyl acetate. In this manner, there was obtained 541 mg. of slightly impure product isolated in fraction Nos. 4-13. A second chromatography run was then made on the latter (i.e., partially purified) material, using 16 g. of silica gel of 70-230 mesh size and eluting this time with an ethyl acetate/triethylamine (9:1 by volume) mixture by taking 10 ml. fractions. The pure triamine was isolated in fractions Nos. 1-2 and these were subsequently combined to afford 358 mg. (13%) of pure pyridin-2,3-diyl-dimethylenebis(1,1'-piperidine) as the free base. Conversion of the latter triamine base compound to the corresponding crystalline hydrated dimaleate salt was then accomplished in the usual manner by treatment with excess maleic acid dissolved in diethyl ether, followed by recrystallization of the isolated salt product from isopropyl alcohol to give analytically pure pyridine-2,3-diyl-dimethylenebis(1,1'-piperidine) dimaleate 0.25 hydrate, m.p. 166°-167° C.

Anal. Calcd. for $C_{17}H_{27}N_3 \cdot 2C_4H_4O_4 \cdot 0.25H_2O$: C, 58.85; H, 7.02; N, 8.24. Found: C, 58.72; H, 6.81; N, 8.23.

A sample of the pure dimaleate salt was then converted back to the free base compound in the same manner as that described for the corresponding salt in Preparation A (except that 4 N aqueous potassium hydroxide was the reagent employed in this particular instance) to afford a viscous oil, which proved to be pure pyridin-2,3-diyl-dimethylenebis(1,1'-piperidine) as attested to by nuclear magnetic resonance data.

EXAMPLE VII

The following organic diamine base compounds are prepared by employing the procedures described in the previous Examples (as well as in Preparations A-P), starting from readily available materials in each instance:

[1,2-phenylenebis(methylene)]bisamine
[1,4-phenylenebis(methylene)]bis(di-n-butylamine)
[1,2-phenylenebis(methylene)]bis(monomethylamine)
[1,3-phenylenebis(methylene)]bis(mono-n-butylamine)
1-(2-aminomethylphenylmethyl)pyrrolidine
1-[2-(N,N-dimethylamino)phenylmethyl]piperidine
4-(2-aminomethylphenylmethyl)morpholine
4-[2-aminomethylphenylmethyl]thiomorpholine
2,3-dihydro-2-(2-aminomethylphenylmethyl)-1H-isoindole
2,3-dihydro-2-[2-(N,N-dimethylamino)methylphenylmethyl]-1H-isoindole
1,2,3,4-tetrahydro-2-(2-aminomethylphenylmethyl)isoquinoline
4-(2-aminomethylphenylmethyl)aminopyridine
4-[2-(N,N-dimethylamino)phenylmethyl]aminopyridine
4-[2-(1-piperidinomethyl)phenylmethyl]aminopyridine
4,4'-[1,2-phenylenebis(methylene)]bis(aminopyridine)
2,2'-[1,4-phenylenebis(methylene)]bis(aminopyridine)
1,1'-[1,3-phenylenebis(methylene)]bishomopiperidine
1,1'-[3-fluoro-1,2-phenylenebis(methylene)]bispyrrolidine
1,1'-[4-chloro-1,2-phenylenebis(methylene)]bispiperidine
4,4'-[4-bromo-1,2-phenylenebis(methylene)]bismorpholine
1,1'-[3-nitro-1,2-phenylenebis(methylene)]bispiperidine
1,1'-[3-methyl-1,2-phenylenebis(methylene)]bispiperidine
1,1'-[4-(n-butyl)-1,2-phenylenebis(methylene)]bispiperidine
1,1'-[3-(n-butoxy)-1,2-phenylenebis(methylene)]bispiperidine
1,1'-[1,3-phenylenebis(methylene)]bis(2,3-dihydro-1H-isoindole)
1,1'-[1,4-phenylenebis(methylene)]bis(1,2,3,4-tetrahydroisoquinoline)
2,3-dihydro-2-[3-(4-pyridylaminomethyl)phenylmethyl]-1H-isoindole
2,3-dihydro-2-[4-(2-pyridylaminomethyl)phenylmethyl]-1H-isoindole
2,3-dihydro-3-[2-(1-piperidinomethyl)phenylmethyl]-1H-isoindole
2,3-dihydro-2-[4-(1-piperidinomethyl)phenylmethyl]-1H-isoindole
2,3-dihydro-2-[3-(4-morpholinomethyl)phenylmethyl]-1H-isoindole
[trans-1,2-cyclohexylenebis(methylene)]bisamine
[trans-1,2-cyclohexylenebis(methylene)]bis(dimethylamine)

[trans-1,2-cyclohexylenebis(methylene)]bis(di-n-butylamine)
[trans-1,2-cyclohexylenebis(methylene)]bis(monomethylamine)
[trans-1,2-cyclohexylenebis(methylene)]bis(mono-n-butylamine)
4,4'-[trans-1,2-cyclohexylenebis(methylene)]bis(aminopyridine)
1,1'-[trans-1,2-cyclohexylenebis(methylene)]bispyrrolidine
1,1'-[trans-1,2-cyclohexylenebis(methylene)]bishomopiperidine
4,4'-[trans-1,2-cyclohexylenebis(methylene)]bismorpholine
4,4'-[trans-1,2-cyclohexylenebis(methylene)]bisthiomorpholine
[5-norbornen-trans-2,3-ylenebis(methylene)]bisamine
[5-norbornen-trans-2,3-ylenebis(methylene)]bis(monoisopropylamine)
[5-norbornen-trans-2,3-ylenebis(methylene)]bis(di-n-butylamine)
3,3'-[5-norbornen-trans-2,3-ylenebis(methylene)]bis(aminopyridine)
1,1'-[5-norbornen-trans-2,3-ylenebis(methylene)]bispyrrolidone
1,1'-[5-norbornen-trans-2,3-ylenebis(methylene)]bishomopiperidine
4,4'-[5-norbornen-trans-2,3-ylenebis(methylene)]bismorpholine
4,4'-[5-norbornen-trans-2,3-ylenebis(methylene)]bisthiomorpholine
[2,5-furandiylbis(methylene)]bisamine
[3,4-furandiylbis(methylene)]bis(dimethylamine)
[2,5-furandiylbis(methylene)]bis(monomethylamine)
[2,5-furandiylbis(methylene)]bis(di-n-butylamine)
4,4'-[3,4-furandiylbis(methylene)]bis(aminopyridine)
1,1'-[3,4-furandiylbis(methylene)]bishomopiperidine
4,4'-[3,4-furandiylbis(methylene)]bismorpholine
4,4'-[2,5-furandiylbis(methylene)]bisthiomorpholine
2,2'-[2,5-furandiylbis(methylene)]bis(2,3-dihydro-1H-isoindole)
[2,5-thiophenediylbis(methylene)]bisamine
[3,4-thiophenediylbis(methylene)]bis(dimethylamine)
[2,5-thiophenediylbis(methylene)]bis(monomethylamine)
[3,4-thiophenediylbis(methylene)]bis(monoisobutylamine)
[2,5-thiophenediylbis(methylene)]bis(di-n-butylamine)
2,2'-[2,5-thiophenediylbis(methylene)]bis(aminopyridine)
1,1'-[3,4-thiophenediylbis(methylene)]bispyrrolidine
1,1'-[2,5-thiophenediylbis(methylene)]bispiperidine
1,1'-[3,4-thiophenediylbis(methylene)]bishomopiperidine
1,1'-[2,5-thiophenediylbis(methylene)]bismorpholine
2,2'-[2,5-thiophenediylbis(methylene)]bis(1,2,3,4-tetrahydroisoquinoline)
indan-1,3-diylbisamine
indan-1,3-diylbis(dimethylamine)
indan-1,3-diylbis(monomethylamine)
indan-1,3-diylbis(mono-n-butylamine)
indan-1,3-diylbis(di-n-butylamine)
indan-1,3-diylbis(4,4'-aminopyridine)
indan-1,3-diylbis(1,1'-pyrrolidine)
indan-1,3-diylbis(1,1'-homopiperidine)
indan-1,3-diylbis(4,4'-morpholine)
indan-1,3-diylbis(4,4'-thiomorpholine)
indan-1,3-diylbis[2,2'-(2,3-dihydro-1H-isoindole)]
indan-1,3-diylbis[2,2'-(1,2,3,4-tetrahydroisoquinoline)]
4-fluoroindan-1,3-diylbis(dimethylamine)
5-chloroindan-1,3-diylbis(monomethylamine)
5-bromoindan-1,3-diylbis(monoisobutylamine)
5-nitroindan-1,3-diylbis(di-n-butylamine)
5-cyanoindan-1,3-diylbis(3,3'-aminopyridine)
4-methylindan-1,3-diylbis(1,1'-pyrrolidine)
5-(n-butyl)indan-1,3-diylbis(1,1'-piperidine)
4-methoxyindan-1,3-diylbis(1,1'-homopiperidine)
5-(n-butoxy)indan-1,3-diylbis(4,4'-morpholine)
pyridin-2,3-diyldimethylenebisamine
pyridin-2,3-diyldimethylenebis(dimethylamine)
pyridin-2,4-diyldimethylenebis(monomethylamine)
pyridin-2,5-diyldimethylenebis(monoisobutylamine)
pyridin-2,6-diyldimethylenebis(di-n-butylamine)
pyridin-2,5-diyldimethylenebis(2,2'-aminopyridine)
pyridin-2,3-diyldimethylenebis(1,1'-pyrrolidine)
pyridin-2,4-diyldimethylenebis(1,1'-homopiperidine)
pyridin-2,3-diyldimethylenebis(4,4'-morpholine)
pyridin-2,4-diyldimethylenebis(4,4'-thiomorpholine)
pyridin-2,5-diyldimethylenebis[2,2'-(2,3-dihydro-1H-isoindole)]
pyridin-2,6-diyldimethylenebis[2,2'-(1,2,3,4-tetrahydroisoquinoline)]

EXAMPLE VIII

The non-toxic hydrohalide acid addition salts of each of the previously reported organic diamine base compounds of this invention, such as the corresponding hydrochloride, hydrobromide and hydriodide salts, are each individually prepared by first dissolving the respective organic base compound in absolute ether followed by the introduction of the appropriate hydrohalide gas into the reaction solution until saturation of same is complete with respect to said gas, whereupon the desired acid addition salt soon precipitates from said solution. In this way, 5.0 g. of 1,1'-[1,2-phenylenebis(methylene)]bispiperidine, obtained as a free base product in Preparation A, is converted via dry hydrogen chloride gas to the corresponding dihydrochloride acid addition salt in substantially quantitative yield.

EXAMPLE IX

The nitrate, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts of each of the aforementioned organic diamine base compounds reported previously are each prepared by dissolving the proper molar amounts of the respective acid and base in separate portions of ethanol and then mixing the two solutions together, followed by the addition of diethyl ether to the resultant mixture in order to effect precipitation of the desired acid addition therefrom. In this manner, equimolar amounts of 2,3-dihydro-2-[2-(1-piperidinomethyl)phenylmethyl]-1H-isoindole and concentrated sulfuric acid react to afford the corresponding sulfuric acid addition salt. In like manner, each of the other salts is similarly prepared.

EXAMPLE X

The quaternary ammonium salts of each of the previously reported organic diamine base compounds of this invention are each individually prepared by treating the respective organic diamine base with the desired reagent of choice in this connection, such as methyl iodide, ethyl bromide, n-propyl iodide, allyl chloride, n-hexyl bromide, cyclopentyl iodide, benzyl chloride, m-xylyl bromide p-chlorobenzyhydryl chloride, dimethyl sulfate, dimethyl sulfite, diethyl sulfate, methyl benzenesulfonate or ethyl p-toluenesulfonate, as the case may be, according to the procedure described by Clarke et al., as reported in the *Journal of the American Chemical Society*, Vol. 55, p. 4571 (1933). In this way, 1.0 g. of 2,3-dihydro-2-[2-(4-morpholinomethyl)phenylmethyl]-1H-isoindole and ethyl bromide react to afford the corresponding ethyl quaternary ammonium salt, viz., 4,4'-diethyl-2,3-dihydro-2-[2-(4-morpholinomethyl)phenylmethyl]-1H-isoindole dibromide. In like manner, each of the other quaternary salts is similarly prepared.

EXAMPLE XI

A dry solid pharmaceutical composition is prepared by blending the following materials together in the proportions by weight specified below:

| | |
|---|---|
| 1,1'-[1,2-Phenylenebis(methylene)]bispiperidine dimaleate | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each table being of such size that it contains 200 mg. of the active ingredient. Other tablets are also prepared in a similar fashion containing 25, 50 and 100 mg. of the active ingredient, respectively, by merely using the appropriate amount of the organic diamine base compound in each case.

EXAMPLE XII

A dry solid pharmaceutical composition is prepared by combining the following materials together in the proportions by weight indicated:

| | |
|---|---|
| 2,3-Dihydro-2-[2-(1-piperidinomethyl)-phenylmethyl]-1H—isoindole monomaleate | 50 |
| Calcium carbonate | 20 |
| Polyethylene glycol, average molecular weight 4000 | 30 |

The dried mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 250 mg. of the active ingredient.

EXAMPLE XIII

The following organic diamine final products of Preparations A–P and Examples I–VI, respectively, were tested for hypoglycemic activity in terms of their ability to exhibit improved glucose tolerance in groups of five or six male albino rats (each weighing approximately 200–225 g.) of the Charles River strain. No anesthetic was used in this study. The rats were fasted for approximately 18–24 hours prior to administration, a blood sample (zero time), was taken from the tail vein of each animal (having cut at a point just 2 mm. from the tip of the tail) and each animal so examined was thereafter treated with glucose at a dose level of 1.0 g./kg. (made up in 0.9% saline), via the intraperitoneal route of administration, followed by treatment with either saline alone (controls) or the test compound to be administered at dose levels of 100, 50 and 25 mg./kg., respectively, also by the intraperitoneal route of administration. Additional blood samples were then taken from the tail vein in the same manner as before at 0.5, 1, 2 and 3 hour intervals after administration of the drug. The samples were immediately diluted 1:10 (by volume) with 0.1% heparin in 0.9% saline. Blood glucose concentrations (mg./dl.) were then determined by adapting the method of W. S. Hoffman [*Journal of Biological Chemistry*, Vol. 120, p. 51 (1937)] to the Autoanalyzer instrument produced by Technicon Instruments Corporation of Chauncey, N.Y. On this basis, the maximum percent decrease in blood glucose was calculated and reported as such (i.e., as hypoglycemic activity in terms of improved glucose tolerance) for the various compounds listed in the table below:

| Compound | Maximum % Decrease In Blood Glucose | | |
|---|---|---|---|
| | 25 mg./kg. | 50 mg./kg. | 100 mg./kg. |
| Product of Preparation A | 35 | — | 59 |
| Product of Preparation B | — | — | 15 |
| Product of Preparation C | — | — | 26 |
| Product of Preparation D | — | — | 14 |
| Product of Preparation E | — | — | 21 |
| Product of Preparation F | — | — | 12 |
| Product of Preparation G | — | — | 11 |
| Product of Preparation H | — | — | 22 |
| Product of Preparation I | 13 | — | — |
| Product of Preparation J | — | 28 | 41 |
| Product of Preparation K | — | — | 7 |
| Product of Preparation L | — | — | 22 |
| Product of Preparation M | — | 47 | — |
| Product of Preparation N | — | 57 | — |
| Product of Preparation O | 11 | — | 44 |
| Product of Preparation P | — | — | 19 |
| Product of Example I | 16 | — | — |
| Product of Example II | — | — | 34 |
| Cis-isomer of Ex. III | — | 21 | — |
| Trans-isomer of Ex. III | — | 7 | — |
| Product of Example IV | 14 | — | — |
| Product of Example V | — | — | 37 |
| Product of Example VI | — | 14 | — |

EXAMPLE XIV

The organic diamine final products of Preparation A and M, respectively, were tested for hypoglycemic activity in terms of their insulin-releasing properties in separate groups of fasted (18–24 hours) male albino rats (each weighing approximately 200–250 g.) of the Charles River strain. The animals were dosed with phenobarbital at 60 mg./kg. just 30 minutes prior to obtaining blood samples. Blood samples were collected via syringe from the abdominal vein in groups of six animals per treatment. The samples were collected prior to any treatment (zero time) and at 30 and 60 minutes following the administration of glucose at 1.0 g./kg. (made up in 0.9% saline) or glucose plus the test compound at the specified dose. The collected blood was then placed in a heparinized tube, mixed gently and kept on ice until ready for centrifugation. The plasma layer which separated during the course of the centrifugation step was thereafter frozen at −20° C. until assayed for insulin by the method of D. R. Makulu et al., as described in *Diabetes*, Vol. 18, pp. 660–669 (1969). Bovine insulin was taken as the standard reference for comparison purposes. In this manner, the following results were obtained as set forth in the table below where the entries are reported in terms of insulin-release units (with standard deviation) for each compound at either the 0.5 or 1-hour mark:

| Compound | Insulin (U/ml.) ± S.D. | |
|---|---|---|
| | 0.5 HR. | 1.0 HR. |
| Control (glucose) | 61.5 ± 16.2 | 100.0 ± 10.1 |
| Prod. of Prep A (75 mg./kg.) | 131.8 ± 11.5 | 82.2 ± 5.6 |
| Control (glucose) | 46 ± 2 | 61 ± 4 |
| Prod. of Prep M (50 mg./kg.) | 78 ± 5 | 38 ± 3 |

EXAMPLE XV

The organic diamine base compounds reported in Example VII are subjected to the test procedure of Example XIII and are all active as hypoglycemic agents for improving the tolerance of glucose at doses corresponding to at least one of the concentration levels previously indicated.

What is claimed is:

1. A compound selected from the group consisting of organic diamine bases of the formula:

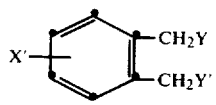

and the pharmaceutically acceptable acid addition and quaternary ammonium salts thereof, wherein
X' is a member selected from the group consisting of nitro, cyano and lower alkoxy; and
Y and Y' are each a member selected from the group consisting of amino, lower N-monoalkylamino, lower N,N-dialkylamino, pyridylamino, pyrrolidino, piperidino, homopiperidino, morpholino, thiomorpholino, 2,3-dihydroisoindolyl and 1,2,3,4-tetrahydroisoquinolyl.

2. A compound as claimed in claim 1 wherein X' is nitro and Y and Y' are each piperidino.

3. A compound as claimed in claim 1 wherein X' is cyano and Y and Y' are each piperidino.

4. A compound as claimed in claim 2 wherein X' is nitro at the 4-position of the molecule.

5. A compound as claimed in claim 3 wherein X' is cyano at the 4-position of the molecule.

6. A pharmaceutical composition suitable for oral administration comprising a pharmaceutically acceptable carrier and an effective blood sugar lowering amount of an oral hypoglycemic agent, said agent being a compound selected from the group consisting of organic diamine bases of the formula

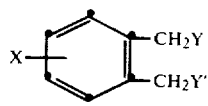

and the pharmaceutically acceptable acid addition and quaternary ammonium salts thereof, wherein
X is a member selected from the group consisting of nitro, cyano, lower alkyl and lower alkoxy and
Y and Y' are each a member selected from the group consisting of amino, lower N-monoalkylamino, lower N,N-dialkylamino, pyridylamino, pyrrolidino, piperidino, homopiperidino, morpholino, thiomorpholino, 2,3-dihydroisoindolyl and 1,2,3,4-tetrahydroisoquinolyl.

7. A composition of claim 6 wherein X is nitro and Y and Y' are each piperidino.

8. A composition of claim 7 wherein X is 4-nitro.

9. A composition of claim 6 wherein X is cyano and Y and Y' are each piperidino.

10. A composition of claim 9 wherein X is 4-cyano.

11. A method for lowering blood sugar in the treatment of a diabetic host, which comprises orally administering to said host an effective blood sugar lowering amount of a compound selected from the group consisting of organic diamine bases of the formula

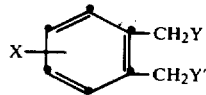

and the pharmaceutically acceptable acid addition and quaternary ammonium salts thereof, wherein
X is a member selected from the group consisting of hydrogen, fluorine, chlorine, bromine, nitro, cyano, lower alkyl and lower alkoxy and
Y and Y' are each a member selected from the group consisting of amino, lower N-monoalkylamino, lower N,N-dialkylamino, pyridylamino, pyrrolidino, piperidino, homopiperidino, morpholino, thiomorpholino, 2,3-dihydroisoindolyl and 1,2,3,4-tetrahydroisoquinolyl.

12. The method of claim 11 wherein X is nitro and Y and Y' are each piperidino.

13. The method of claim 12 wherein X is 4-nitro.

14. The method of claim 11 wherein X is cyano and Y and Y' are each piperidino.

15. The method of claim 14 wherein X is 4-cyano.

* * * * *